United States Patent
Atalar et al.

(10) Patent No.: US 10,641,858 B2
(45) Date of Patent: May 5, 2020

(54) SPATIOTEMPORAL MAGNETIC FIELD MONITORING WITH HALL EFFECT SENSORS DURING THE MRI SCAN

(71) Applicant: Bilkent University, Ankara (TR)

(72) Inventors: Ergin Atalar, Ankara (TR); Soheil Taraghinia, Ankara (TR); Niyazi Koray Ertan, Ankara (TR); Bilal Taşdelen, Osmangazi/Bursa (TR)

(73) Assignee: Bilkent University, Ankara (TR)

(*) Notice: Subject to any disclaimer, the term of this patent is extended or adjusted under 35 U.S.C. 154(b) by 211 days.

(21) Appl. No.: 15/947,160

(22) Filed: Apr. 6, 2018

(65) Prior Publication Data

US 2018/0292502 A1    Oct. 11, 2018

Related U.S. Application Data

(60) Provisional application No. 62/482,464, filed on Apr. 6, 2017.

(51) Int. Cl.
*G01R 33/565*    (2006.01)
*G01R 33/46*    (2006.01)
(Continued)

(52) U.S. Cl.
CPC ........ *G01R 33/56572* (2013.01); *A61B 5/055* (2013.01); *G01R 33/0035* (2013.01);
(Continued)

(58) Field of Classification Search
CPC ............... G01R 33/00; G01R 33/0023; G01R 33/0035; G01R 33/02; G01R 33/06;
(Continued)

(56) References Cited

U.S. PATENT DOCUMENTS 3,982,179 A * 9/1976 Forster ................ G01R 33/022
324/245
5,278,504 A    1/1994 Patrick et al.
(Continued)

FOREIGN PATENT DOCUMENTS

JP    2007-167143 A    7/2007
JP    2007167143    7/2007
(Continued)

OTHER PUBLICATIONS

International Search Report dated Aug. 19, 2016 from PCT/KR2016/005160, pp. 3.
(Continued)

*Primary Examiner* — Hoai-An D. Nguyen
(74) *Attorney, Agent, or Firm* — Nelson Mullins Riley & Scarborough LLP; Thomas J. Engellenner; Reza Mollaaghababa

(57) ABSTRACT

An MRI system includes a gantry having a longitudinal axis (herein "z-axis") and a magnet disposed about the gantry for generating a static magnetic field along the longitudinal axis. Additionally, the system comprises a first gradient magnet for generating a gradient magnetic field along the longitudinal axis; a second gradient magnet for generating a gradient magnetic field along a first transverse direction (herein "x-axis") orthogonal the longitudinal axis; and a third gradient magnet for generating a gradient magnetic field along a second transverse direction (herein "y-axis") orthogonal to the longitudinal axis and the first transverse direction. Magnetic sensors are positioned relative to the gantry to measure gradients of transverse components of magnetic field along one or more of the x, y and z axes. A controller receives measurement signals from the sensors and operates on those signals to determine gradients of the gradient magnetic field along the longitudinal axis.

20 Claims, 11 Drawing Sheets

(51) Int. Cl.
*G01R 33/07* (2006.01)
*G01R 33/00* (2006.01)
*A61B 5/055* (2006.01)
*G01R 33/385* (2006.01)
*A61B 5/05* (2006.01)

(52) U.S. Cl.
CPC ....... *G01R 33/072* (2013.01); *G01R 33/3852* (2013.01); *G01R 33/4625* (2013.01); *G01R 33/4633* (2013.01); *A61B 5/05* (2013.01)

(58) Field of Classification Search
CPC ...... G01R 33/07; G01R 33/072; G01R 33/20; G01R 33/28; G01R 33/288; G01R 33/38; G01R 33/385; G01R 33/3852; G01R 33/44; G01R 33/46; G01R 33/4625; G01R 33/4633; G01R 33/48; G01R 33/54; G01R 33/56; G01R 33/565; G01R 33/56572; A61B 5/00; A61B 5/05; A61B 5/055
USPC .......................................... 324/300, 307, 309
See application file for complete search history.

(56) References Cited

U.S. PATENT DOCUMENTS

| | | | |
|---|---|---|---|
| 5,382,904 | A | 1/1995 | Pissanetzky |
| 5,659,281 | A | 8/1997 | Pissanetzky et al. |
| 6,016,439 | A | 1/2000 | Acker |
| 6,448,773 | B1 | 9/2002 | Zhang |
| 6,472,872 | B1 | 10/2002 | Jack, Jr. et al. |
| 6,501,977 | B1 | 12/2002 | Kimmlingen |
| 6,563,315 | B1 | 5/2003 | Boskamp |
| 6,900,638 | B1 | 5/2005 | Yair et al. |
| 7,202,734 | B1 | 4/2007 | Raab |
| 7,800,368 | B2 | 9/2010 | Vaughan et al. |
| 8,125,225 | B2 | 2/2012 | Koretsky et al. |
| 9,364,663 | B2 * | 6/2016 | Doerr .................. A61N 1/3931 |
| 9,755,576 | B2 | 9/2017 | Perreault |
| 9,923,518 | B2 | 3/2018 | Perreault |
| 10,120,050 | B2 | 11/2018 | Feiweier |
| 10,444,312 | B2 * | 10/2019 | Chung ............... G01R 33/5608 |
| 2001/0024122 | A1 | 9/2001 | Mulder et al. |
| 2004/0162477 | A1 * | 8/2004 | Okamura ................. A61B 5/05 600/409 |
| 2007/0216409 | A1 | 9/2007 | Overweg |
| 2007/0279058 | A1 | 12/2007 | Bulkes et al. |
| 2008/0272784 | A1 | 11/2008 | Harvey et al. |
| 2011/0200243 | A1 * | 8/2011 | Takizawa ........... G01R 33/4824 382/131 |
| 2011/0254551 | A1 | 10/2011 | Leussler |
| 2012/0019251 | A1 * | 1/2012 | Umeda ............ G01R 33/56518 324/322 |
| 2014/0320132 | A1 | 10/2014 | Schmale |
| 2016/0181986 | A1 | 6/2016 | Perreault |
| 2016/0181987 | A1 | 6/2016 | Perreault |
| 2016/0229304 | A1 * | 8/2016 | Bildstein .................. G01D 5/20 |
| 2017/0090000 | A1 * | 3/2017 | Lin .................... G01R 33/3607 |
| 2017/0176389 | A1 * | 6/2017 | Paulson ................ G01N 27/82 |
| 2018/0011156 | A1 | 1/2018 | Atalar |
| 2018/0081003 | A1 | 3/2018 | Atalar |
| 2018/0120393 | A1 | 5/2018 | Atalar |

FOREIGN PATENT DOCUMENTS

| | | |
|---|---|---|
| JP | 2008-168132 A | 7/2008 |
| JP | 2008168132 | 7/2008 |
| JP | 2008264101 | 11/2008 |
| JP | 2008264101 A | 11/2008 |
| JP | 2013000591 | 1/2013 |
| JP | 2013000591 A | 1/2013 |
| JP | 2014-083445 A | 5/2014 |
| JP | 2014083445 | 5/2014 |
| KR | 100900862 | 6/2009 |
| KR | 100900862 B1 | 6/2009 |
| KR | 101503494 | 3/2015 |
| KR | 101503494 B1 | 3/2015 |

OTHER PUBLICATIONS

International Written Opinion dated Aug. 19, 2016 from PCT/KR2016/005160, pp. 6.
Gudino et al., "1.5T On-Coil Current-Mode Class-D (CMCD) Amplifier with Amplitude Modulation Feedback and Voltage-Mode Class-D (VMCD) Preamplifier," Proc. Intl. Soc. Mag. Reson. Med. 18 (2010).
Internatinal Search Report dated Aug. 22, 2016 from PCT/KR2016/005150. pp. 4.
International Written Opinion dated Aug. 22, 2016 from PCT/KR2016/005150, pp. 7.
International Search Report dated Aug. 19, 2016 from PCT/KR2016/005160 (3 pages).
International Written Opinion dated Aug. 19, 2016 from PCT/KR2016/005160 (6 pages).
International Search Report dated Aug. 22, 2016 from PCT Patent Application Serial No. PCT/KR2016/005150 (4 pages).
International Written Opinion dated Aug. 19, 2016 from PCT/KR2016/005150 (6 pages).

* cited by examiner

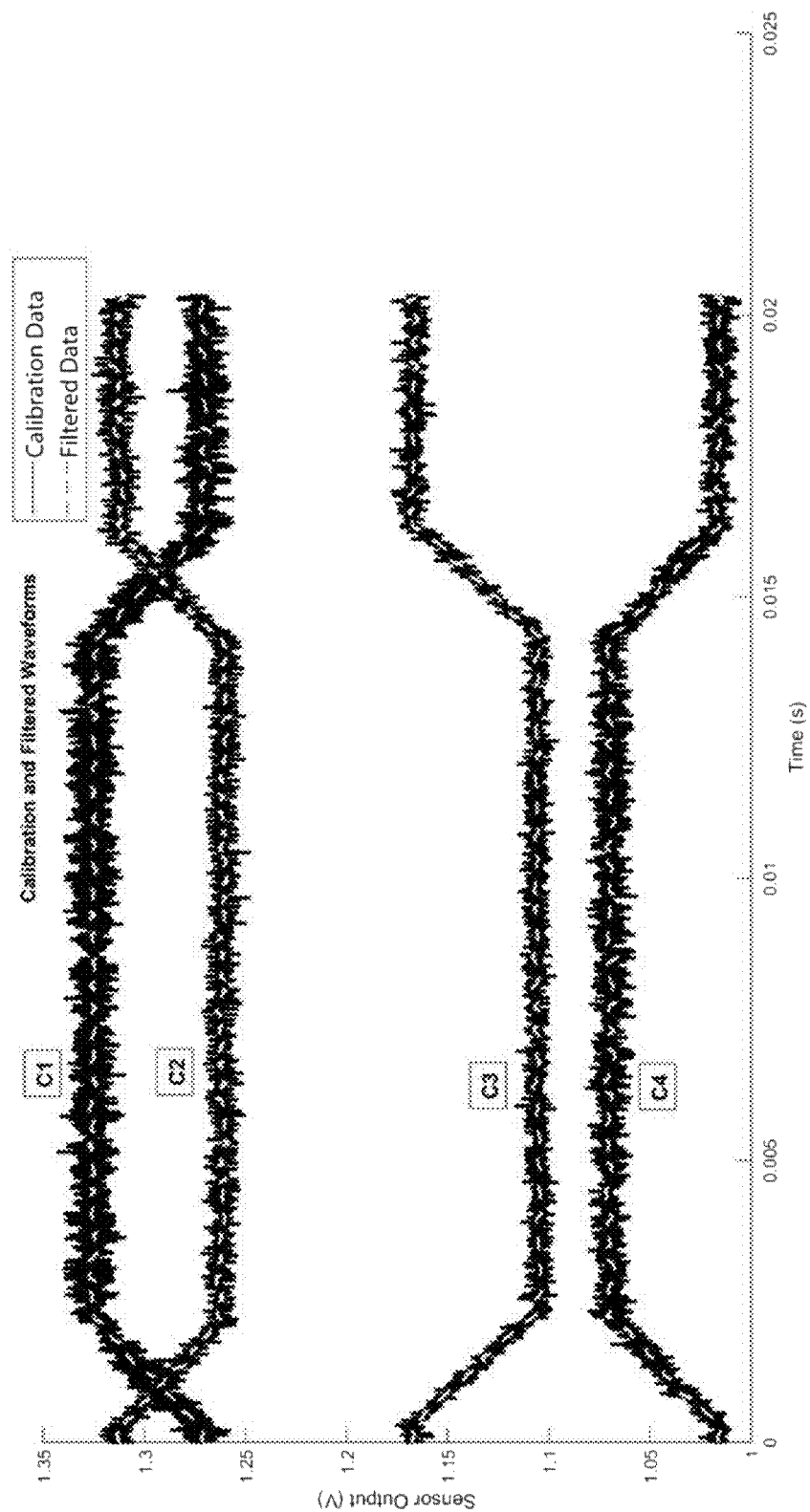

SPATIOTEMPORAL MAGNETIC FIELD MONITORING WITH HALL EFFECT SENSORS DURING THE MRI SCAN

CROSS REFERENCE TO RELATED APPLICATIONS

This application claims benefit of U.S. Provisional Application No. 62/482,464, filed Apr. 6, 2017, the entire contents of which are incorporated herein by reference.

TECHNICAL FIELD

The present invention relates generally to measuring a magnetic field spatiotemporally with magnetic field measurement sensors during, for example, the magnetic resonance imaging (MRI) scan, along with methods, systems, and apparatuses related thereto. The invention can be implemented with various types of measurement sensors including, without limitation, Hall effect sensors.

BACKGROUND

In magnetic resonance imaging (MRI), a scanner system uses three different purpose magnetic fields to obtain an image: the $B_0$ field, gradient fields, and radio frequency (RF) fields. The $B_0$ field is the main magnetic field used by the MRI scanner, and is static in time and homogenous inside the volume of imaging. The $B_0$ field determines the resonance frequency of the atoms depending on the gyromagnetic ratio of the atom. To obtain an image, resonance frequency of the object is spatially modulated by the gradient fields. Modulation may be used to perform particular imaging operations such as slice selection, phase encoding and frequency encoding; however, common purpose of the gradient fields are also used to discriminate different spatial locations by applying additional magnetic fields which has a certain spatial dependency. In conventional MRI scanners, there are three gradient coils used to encode three spatial dimensions: the x-gradient, the y-gradient and the z-gradient. During an imaging sequence, spatial encoding of the object should be changed as a function of time for imaging purposes; therefore gradient coils should be driven dynamically as a function of time and wideband current waveforms are necessary. Finally, the RF field is used to excite the nuclear magnetic spins.

MRI sequences are often designed with generic, idealized magnetic field conditions. Due to hardware imperfections and physical limitations, these ideal conditions are rarely achieved and the magnetic fields applied to a subject can deviate from expectations. The deviations may cause artifacts and distortions in the image; however, as long as the deviations are precisely measured, resulting artifacts and image distortions can be corrected.

Conventional Nuclear Magnetic Resonance (NMR) probes may be used to monitor both spatial and temporal dependency of the magnetic fields to estimate the correct k-space trajectory to be used in the image reconstruction. Although, NMR probes provide effective field monitoring capabilities, the use of NMR probes can be costly. Also, NMR probes are not able to measure the concomitant fields (i.e., fields in the x- and y-direction) simultaneously with the field in the z-direction; rather NMR probes measure each field separately. Although fields in the z-direction are much more important and effective in MRI, fields in the x-y direction also cause artifacts and can be corrected with image processing if known.

SUMMARY

Embodiments of the present invention address and overcome one or more of the above shortcomings and drawbacks, by providing methods, systems, and apparatuses related to measuring a magnetic field spatiotemporally with magnetic field measurement sensors, for example, during the magnetic resonance imaging (MRI) scan.

According to some embodiments, an MRI system includes a gantry for receiving a subject. The gantry has a longitudinal axis (herein "z-axis") and a magnet disposed about the gantry for generating a static magnetic field along the longitudinal axis. Additionally, the system comprises a first gradient magnet for generating a gradient magnetic field along the longitudinal axis; a second gradient magnet for generating a gradient magnetic field along a first transverse direction (herein "x-axis") orthogonal the longitudinal axis; and a third gradient magnet for generating a gradient magnetic field along a second transverse direction (herein "y-axis") orthogonal to the longitudinal axis and the first transverse direction. Magnetic sensors (e.g., Hall effect sensors) are positioned relative to the gantry to measure gradients of transverse components of magnetic field along one or more of the x, y and z axes. The magnetic sensors generate signals indicative of the measured transverse magnetic field gradients. The system includes a controller that receives the signals and operates on the signals to determine gradients of the gradient magnetic field along the longitudinal axis. Additionally, in some embodiments, the controller receives calibration signals from the plurality of sensors in absence of applied magnetic fields and employs the calibration signals for calibrating the magnetic sensors.

In some embodiments, the aforementioned MRI system includes a mechanical holder to which the plurality of magnetic sensors can be mounted. This mechanical holder is positioned relative to the gantry and being configured to provide coordinates of each of the plurality of magnetic sensors along x, y, and z-axes.

In other embodiments, the aforementioned MRI system includes at least one alignment mechanism for aligning at least one of the plurality of magnetic sensors along any of the x and y-axes for measuring magnetic fields along the axes. For example, in one embodiment, the alignment mechanism comprises a piezoelectric actuator coupled to the at least one of the magnetic sensors. This alignment mechanism may be controlled, for example, by the controller. For example, in one embodiment, the controller instructs the alignment mechanism to adjust an orientation of the at least one sensor based on an output voltage signal generated by the least one sensor. The alignment mechanism may rotate the sensor in response to a control signal from the controller so as to align the at least one sensor along on of the x and y-axes.

According to another aspect of the present invention, a method for measuring a gradient magnetic field in a magnetic resonance system includes positioning a plurality of magnetic sensors relative to a longitudinal axis ("z-axis") of a gantry and using the plurality of magnetic sensors to collect measurements. These measurements include a measurement of a gradient magnetic field along a first transverse direction ("x-axis") orthogonal to the longitudinal axis, and a measurement of a gradient magnetic field along a second transverse direction ("y-axis") orthogonal to the longitudinal axis and the first transverse direction. Based on the measurement of the gradient magnetic field along the x-axis and the measurement of a gradient magnetic field along the y-axis, a measurement of a gradient magnetic field along the z-axis is determined.

According to other embodiments of the present invention, an MRI system includes a plurality of magnetic sensors and one or more computers. The magnetic sensors are positioned relative to a longitudinal axis (i.e., the "z-axis") of a gantry. The magnetic sensors are configured to collect measurements during an MRI scan. These measurements include a measurement of a gradient magnetic field along a first transverse direction (i.e., "x-axis") orthogonal to the longitudinal axis, and a measurement of a gradient magnetic field along a second transverse direction (i.e., "y-axis") orthogonal to the longitudinal axis and the first transverse direction. In one embodiment, the y-axis is orthogonal to the x-axis. The computers are configured to determine a measurement of a gradient magnetic field along the z-axis based on the measurement of the gradient magnetic field along the x-axis and the measurement of the gradient magnetic field along the y-axis.

In some embodiments, the computers are further configured to estimate a k-space trajectory of the MRI scan based on the measurement of the gradient magnetic field along the x-axis and the measurement of the gradient magnetic field along the y-axis. Then computers use the k-space trajectory to reconstruct images based on k-space data acquired during the MRI scan. Additionally, in some embodiments, the computers are further configured to estimate patient motion data based on the measurement of the gradient magnetic field along the x-axis and the measurement of the gradient magnetic field along the y-axis. Then, the patient motion data may be used to perform motion correction on the one or more images.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there are shown in the drawings embodiments that are presently preferred, it being understood, however, that the invention is not limited to the specific instrumentalities disclosed. Included in the drawings are the following Figures:

FIG. 9A shows calibration data for each sensor when a z gradient is applied, according to some embodiments;

DETAILED DESCRIPTION

The following disclosure describes the present invention according to several embodiments directed at methods, systems, and apparatuses that perform spatiotemporal magnetic field monitoring with hall effect sensors during the magnetic resonance imaging (MRI) scan. More specifically, Hall effect sensors are used to monitor the spatiotemporal field dynamics of the gradient fields in MRI. Measurement of the z component of the magnetic field ($B_z$) requires very large dynamic range for the Hall effect sensors due to superposition of encoding fields with main magnetic field ($B_0$). To address this requirement, the techniques described herein measure the transverse components of the magnetic field in several spatial positions to reconstruct spatiotemporal dependency of Bz. In other words, the transverse magnetic fields can be measured because a static magnetic field does not cause saturation of the sensors and additionally, the spatial map of the magnetic field may be reconstructed up to a desired order of spherical harmonics depending on the number of sensors.

Figure 1:
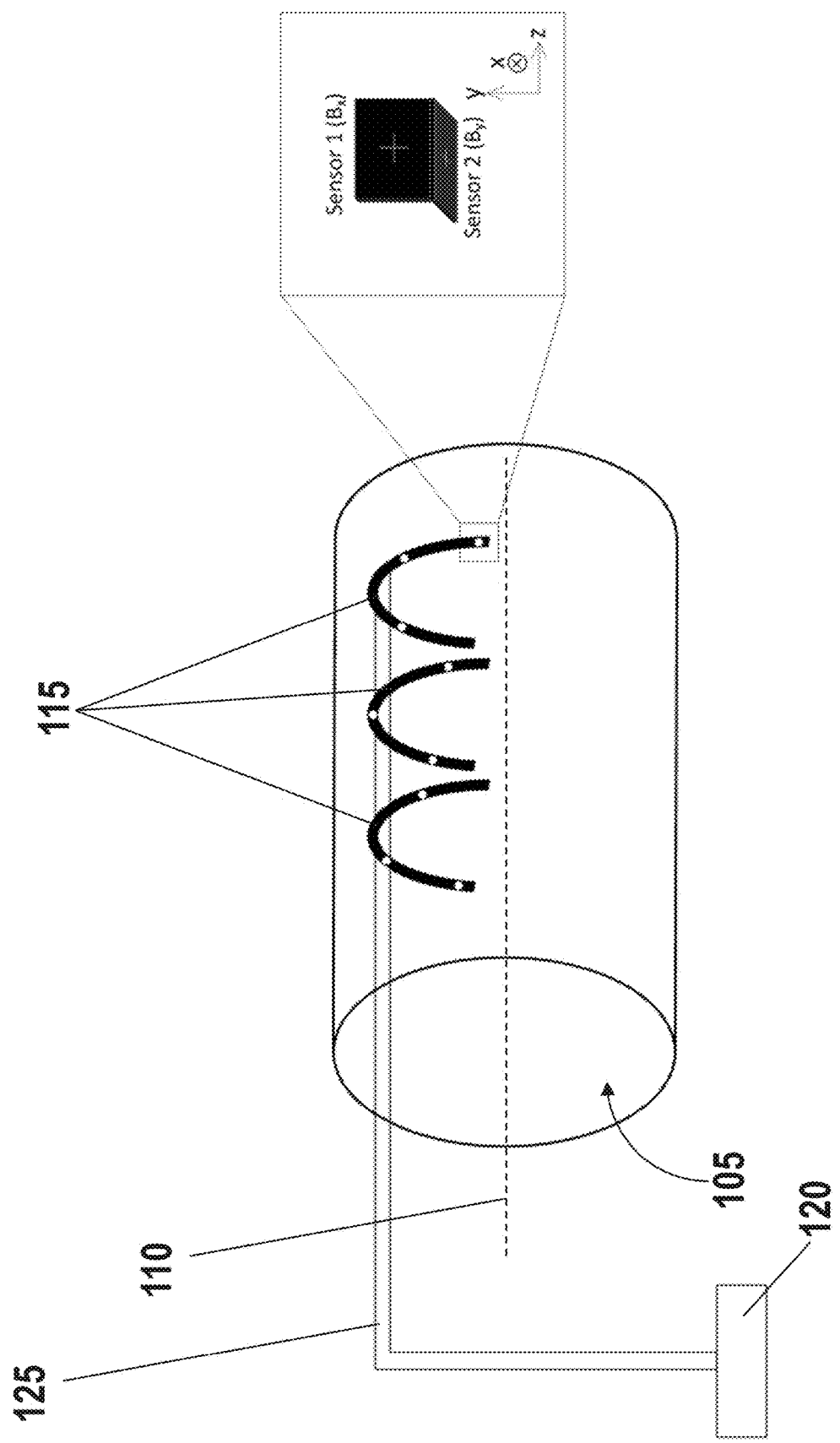
FIG. 1 provides an overview of how spatiotemporal magnetic field monitoring may be implemented in some embodiments.

FIG. 1 provides an overview of how spatiotemporal magnetic field monitoring may be implemented, in some embodiments. It should be noted that this example illustrates embodiments of the present invention on a conceptual level and a more detailed description of an MRI scanner system is described below with respect to FIG. 10. The bore 105 of the MRI scanner is sized to receive a subject. There are various types of bore designs known in the art (e.g., normal, wide bore, open bore, etc.) and, in general any bore design can be used in conjunction with the techniques described here.

A magnet (not shown in FIG. 1) is disposed about the bore 105 to generate a static magnetic field along the longitudinal axis 110 of the bore 105. As described in further detail below with respect to FIG. 10, an MRI scanner has three gradient coils for generating gradient magnetic fields. Each coil may be driven by an independent power amplifier. A first gradient coil generates a gradient magnetic field along the longitudinal axis 110. A second gradient coil generates a gradient magnetic field along a first transverse direction (herein "x-axis") orthogonal the longitudinal axis 110. Finally, a third gradient coil generates a gradient magnetic field along a second transverse direction (herein "y-axis") orthogonal to the longitudinal axis 110 and the transverse direction.

A plurality of magnetic sensors 115 are positioned relative to the bore 105 to measure magnitude of the magnetic field at multiple points. From these multiple measurements, the spherical harmonic coefficients of the x- and y-oriented magnetic fields are estimated (as described in further detail below). Later, using the Maxwell equations, the spherical order coefficients of the z-oriented field are obtained. A support structure 125 is used to hold the plurality of magnetic sensors 115 in a fixed position so that, after initial calibration, the plurality of magnetic sensors 115 will stay perpendicular to z position when they are moved to other position. In some embodiments, the support structure 125 is positioned to avoid physical contact with the scanner in order to minimize movement of the support structure 125 due to vibration modulation of the scanner. An additional apparatus may be connected to holder in order to determine the exact position of the sensors.

Figure 2:
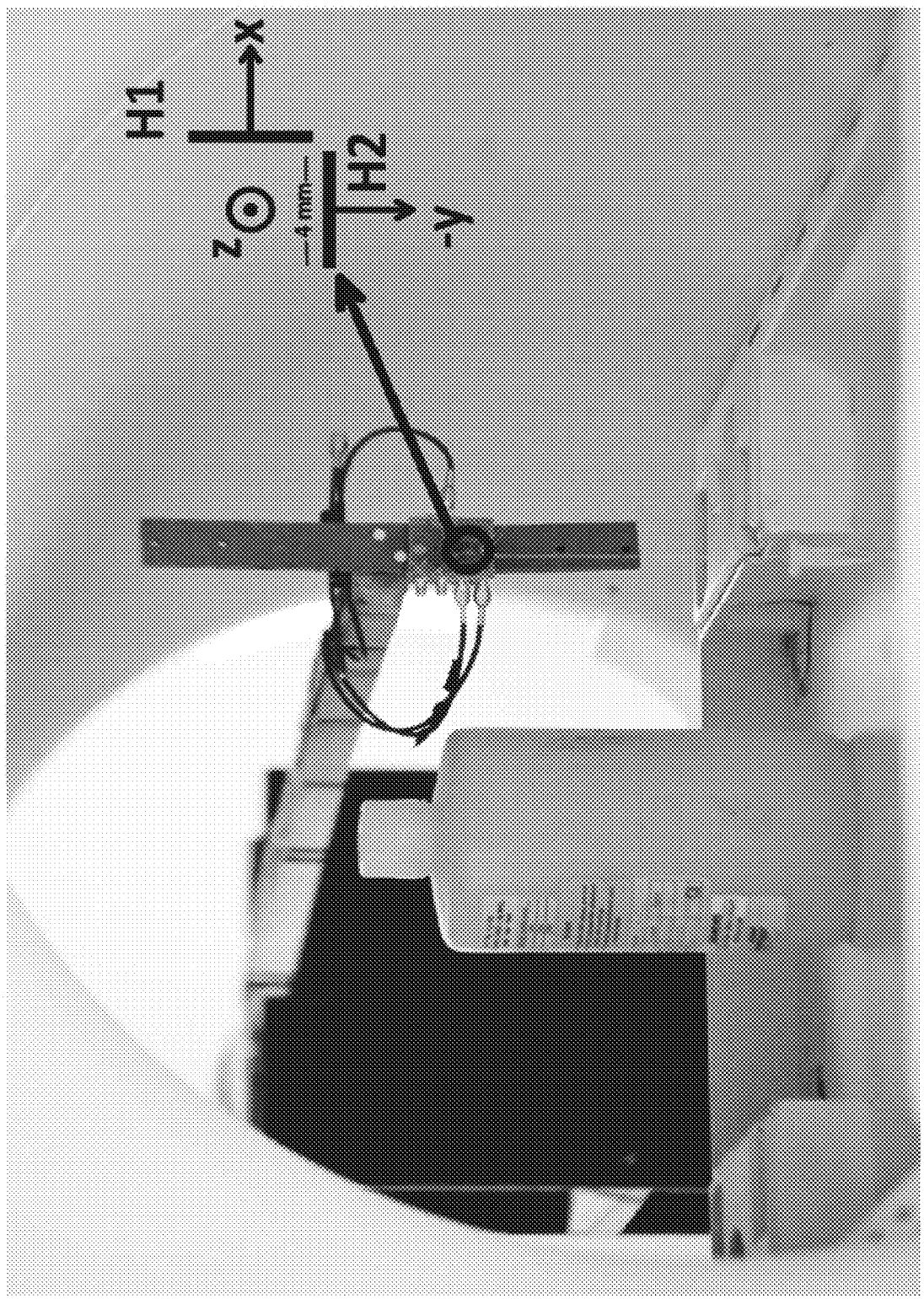
FIG. 2 shows an experimental setup including two Hall effect sensors.

In general, the magnetic sensors 115 can perform any magnetic field measurement method that directly measures the transverse component and approximates the longitudinal component. For example, in one embodiment, the magnetic sensors are Hall effect sensors. As would be understood by one skilled in the art, the Hall effect is the production of a voltage difference across an electrical conductor when a magnetic field is applied in a direction perpendicular to that of the flow of current. This voltage difference is referred to as the "Hall voltage." A Hall effect sensor is a transducer that measures the Hall voltage across the two faces of the transducer when it is placed in a magnetic field (in this case, within the bore 105). FIG. 2 shows an experimental setup including two groups Hall effect sensors (labeled H1 and H2). The group of H1 sensors comprises a plurality of sensors displaced along the x direction to measure the x-gradient. Similarly, the group of H2 sensors comprises a plurality of sensors displaced along the y direction to measure the y-gradient. In this example, the sensors are manually aligned perpendicular to the z-axis by adjusting the sensor output to 0 Volts. In general, any type of Hall effect sensor may be employed with the techniques described herein. For example, in one embodiment, commercially available Hall effect sensors (e.g., Texas Instruments DRV5053, Allegro A1366LKT-10-T) are employed. The quality of the sensor can vary from embodiment-to-embodiment as well. For example, in some embodiments, sensors with 20 kHz bandwidth and 23 mV/mT sensitivity are used. In other embodiments, sensors with 120 kHz bandwidth and 10V/mT sensitivity are used.

The plurality of magnetic sensors 115 shown in FIG. 1 may be arranged based on factors such as the required spatial resolution of the measurements or order of the spherical harmonics. The alignment angle between the x and y direction can vary based on mechanical or geometric factors, as long as the z-axis remains orthogonal. For example, in some embodiments, the magnetic sensors are aligned at a 45 degree angle between x and y direction.

In order to calibrate the system, some parameters related to sensors may be measured before they are embedded in the system to increase the accuracy of the system. First, due to its potential variance during operations, output voltage of the sensors to zero magnetic field may be calibrated. Second, sensitivity of the sensors may be measured outside of the system with a reliable magnetic field source and voltage measurement device such as oscilloscope to determine the exact sensitivity of the voltage. The output voltage of the sensors can also vary as a function of frequency and frequency response can be calculated. The frequency response can be used to deconvolve the output signals to further increase the accuracy of the system.

Where Hall effect sensors are employed, the locations of the plurality of magnetic sensors 115 should be known in order to solve spherical harmonics equations. There are various ways of measuring the sensor location. In some embodiments, small phantoms are imaged using the MRI to determine the locations of the phantoms in the MR scanner coordinate system. Sensor locations can then be measured at the production stage of the mechanical cover or they can be measured with any conventional measurement technique generally known in the art. In other embodiments, a mechanical holder for the sensors is positioned relative to said bore and configured to provide coordinates of each of the sensors along x, y, and z-axes. This mechanical holder may be mounted, for example, on a conventional RF receive coil's mechanical holder. In still other embodiments, one or more electrical devices are used to measure the location of the sensors such as visible and non-visible optics, gyroscopes etc.

Figure 10:
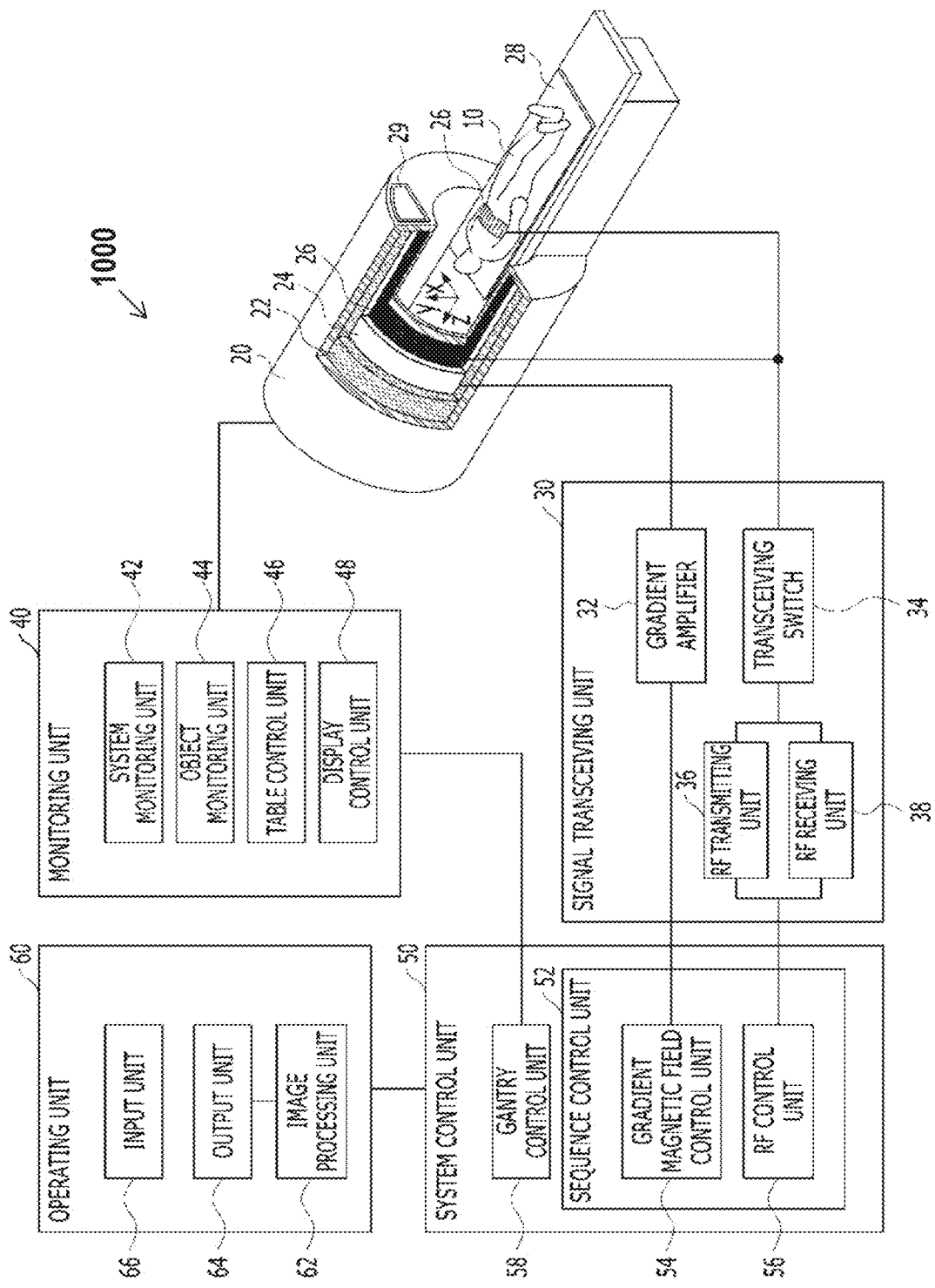
FIG. 10 is a block diagram illustrating a MRI scanner system according to an embodiment of the present disclosure.

Mechanical vibration of the MRI scanner can also vibrate the plurality of magnetic sensors during scanning. In turn, the sensor vibration can cause modulation of the sensors with the z direction and result in a changing magnetic field due to changing angle with the main magnetic field. Sensors should not physically contact with the MRI scanner because vibration of the scanner can modulate the angle of the sensors in both longitudinal and transverse angles. Modulation in the z direction has severe effects on the main magnetic field $B_0$. This effect may be reduced by placing the sensors in a mechanical cover with no direct physical contact with the MRI scanner system (as shown in FIG. 10). In other embodiments, a mechanical cover is placed in physical contact with one or more components of the scanner (e.g., an RF receive coil) while avoiding contact with other components. Alternately, the mechanical holder used to hold the sensor may be designed with strong mechanical properties to avoid vibration or the vibration effect might be digitally cancelled.

Continuing with reference to FIG. 1, controller 120 receives signals from the magnetic sensors and performs one or more operations (described in greater detail below) to determine gradients of the longitudinal magnetic field for one or more locations in the bore 105. In this way, one or more of the magnetic fields within the MR volume can be measured. Magnetic fields that are not measured can be estimated. For example, in one embodiment, the x and y directions of the magnetic field inside the MR volume are measured. Then, an estimation is performed for the z-component of the field for x-gradient coil, y-gradient coil and z-gradient coil and shim coils.

As an example of the operations performed by the controller 120 in embodiments where the plurality of magnetic sensors 115 are Hall effect sensors, consider the following. The Hall effect sensors are used to measure directly $B_z$ inside the bore 105; however field deviations are on the order of parts-per-million of the $B_0$ need to be monitored because such deviations can cause artifacts in the images. Such a high dynamic range results in either very low sensitivity or saturation of the MRI sensor. Ideally, when Hall elements are aligned to measure concomitant fields, there will be no interference with the main magnetic fields which will not cause saturation and high sensitivity can be maintained. Additionally, if the direction of the current in Hall element is aligned with the z-direction inside the MRI scanner, the wavelength at the gradient frequencies are very long (~104 m), Maxwell equations can be written as follows:

$$\nabla \times B = \hat{x}\left(\frac{\partial B_z}{\partial y} - \frac{\partial B_y}{\partial z}\right) + \hat{y}\left(-\frac{\partial B_z}{\partial x} + \frac{\partial B_x}{\partial z}\right) + \hat{z}\left(\frac{\partial B_y}{\partial x} - \frac{\partial B_x}{\partial y}\right) = \hat{z}\mu_0 J \quad (1)$$

$$\frac{\partial B_z}{\partial y} = \frac{\partial B_y}{\partial z} \frac{\partial B_z}{\partial x} = \frac{\partial B_x}{\partial z}$$

$$\nabla B = \frac{\partial B_x}{\partial x} + \frac{\partial B_y}{\partial y} + \frac{\partial B_z}{\partial z} = 0 \quad (2)$$

The last partial derivative of the Bz can be determined from the zero divergence condition as in Equation 2. Therefore, knowledge of transverse fields is adequate to determine the partial derivatives of the $B_z$ (i.e., $\nabla B_z$). However, the spatial direct current (DC) component is not included in this formulation. This DC component can be calculated by assuming that all magnetic fields decay at a distant location as an additional equation. Alternatively, the spatially constant term (i.e., the DC component) may be determined using an additional NMR probe for the direct measurement of the frequency. Because the DC term is not used to calculate $B_z$, measurement at three points is adequate to measure first order spherical harmonics of $B_x$ and $B_y$. Note that, at each point there are two sensors oriented for x- and y-directions respectively; therefore, their physical locations are very close but not exactly same. The sensors can even be physically separated by some distance; as long as there are enough sensors for each direction to allow reconstruction of the $B_x$ and $B_y$ fields, the $B_z$ field can be reconstructed. Afterwards, using Equations 1 and 2, $B_z$ can be calculated up to same order spherical harmonics with $B_x$ and $B_y$. When spherical harmonic terms with unknown coefficients are inserted into Equations 1 and 2, unknown coefficients can be solved by trivial algebraic and analytical expressions or matrix inversion techniques generally known in the art.

Alignment of the plurality of sensors 115 with the z direction is very critical because even few degrees of coupling are enough to saturate the sensors due to the high static field. For example, in the 1 Volt measurement range, 23 mV/mT sensitivity and 3 Tesla $B_0$ results in a 0.83 degree coupling, which is enough to completely saturate the sensor and similarly this leads to a decrease in the accuracy of the transverse measurements because measurements are multiplied with the cosine of the alignment angle (i.e., $\cos(\theta)$).

To address the alignment issues discussed above, various strategies may be employed. For example, in some embodiments, the sensors are manually aligned. In other embodiments, sensors are placed on a mechanical holder which is compatible with the MRI coordinate system. For example in one embodiment, sensors are placed to a precisely manufactured 3D printed cube which has holes on the four sides. Sensors exactly fit to the holes in the cube, which provides the 90 degree alignment of the sensors in the transverse direction. Even if sensors are not aligned in the transverse plane, it is possible to calibrate the system by applying currents to conventional MRI gradient coils. Furthermore, in these embodiments, there may be an additional hole inside the cube where a wire can be placed. When DC current is applied to a wire in the hole, the wire is aligned with z direction due to Lorentz Force induced by the main magnetic field. In this way, alignment in the longitudinal direction can be satisfied.

Figure 3:
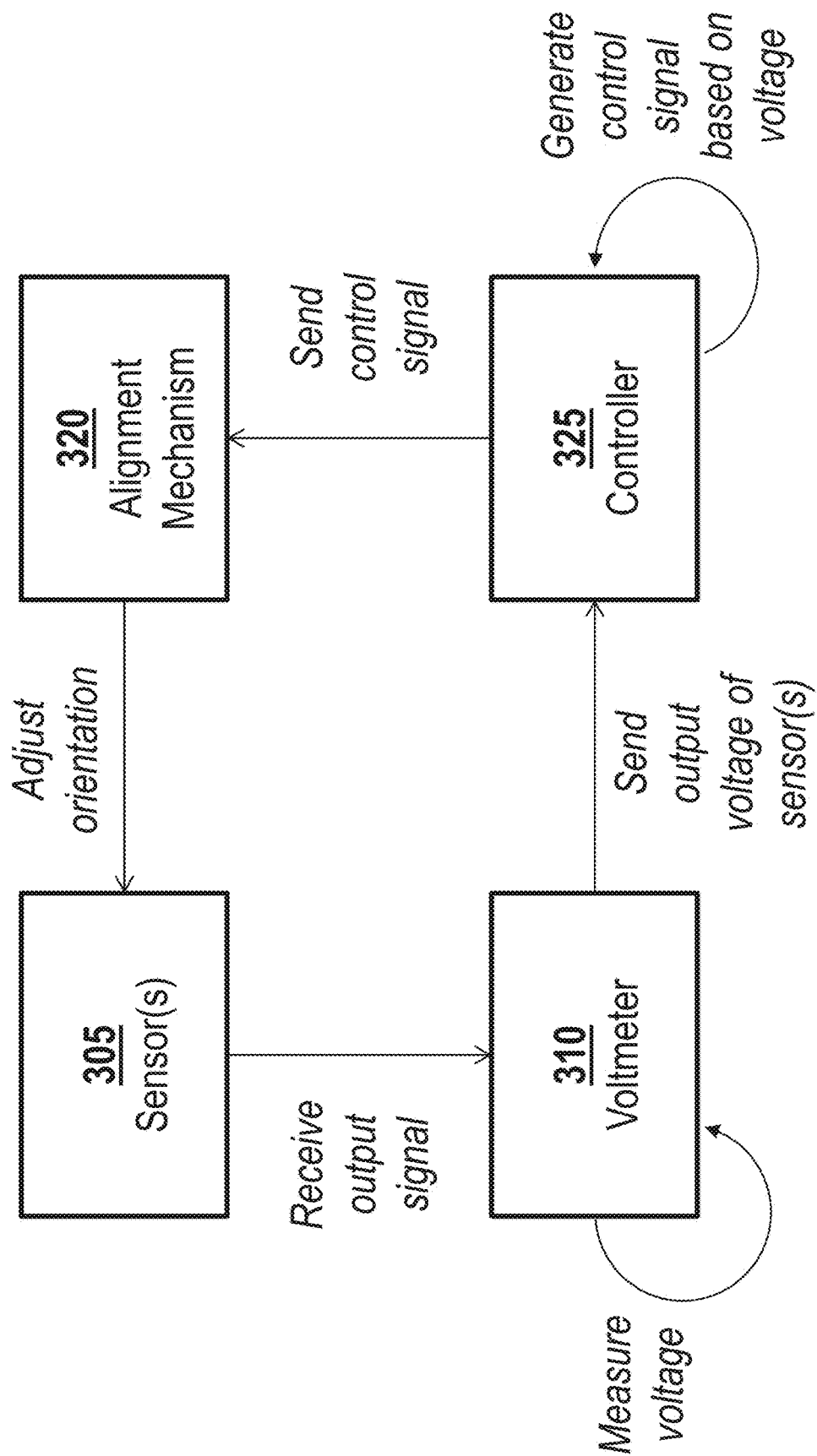
FIG. 3 shows a framework for aligning magnetic sensors, according to some embodiments of the present invention.

In other embodiments, an alignment mechanism placed outside of the scanner is used actively to align the sensors by receiving a feedback signal from the output voltage of a sensor because the zero magnetic field output voltage of the sensors are already known. A framework for performing this method is shown in FIG. 3. Note that the framework depicted in FIG. 3 is a loop; thus, the sensors can continually be monitored and re-aligned, as necessary, during operation. The output signal from the sensors 305 is received by a voltmeter 310. The voltmeter 310 measures the voltage of the output signal and sends the measurements to a controller 325. Next, the controller 325 generates a control signal for the alignment mechanism 320 based on the voltage measurement. The alignment mechanism 320 then adjusts the orientation of the sensors 305 according to the control signal received from the controller 325 so as to ensure that the output voltage of the sensors is at the desired value and within the desired range. The alignment mechanism 320 may be, for example, a piezoelectric device or any type motor.

Figure 4:
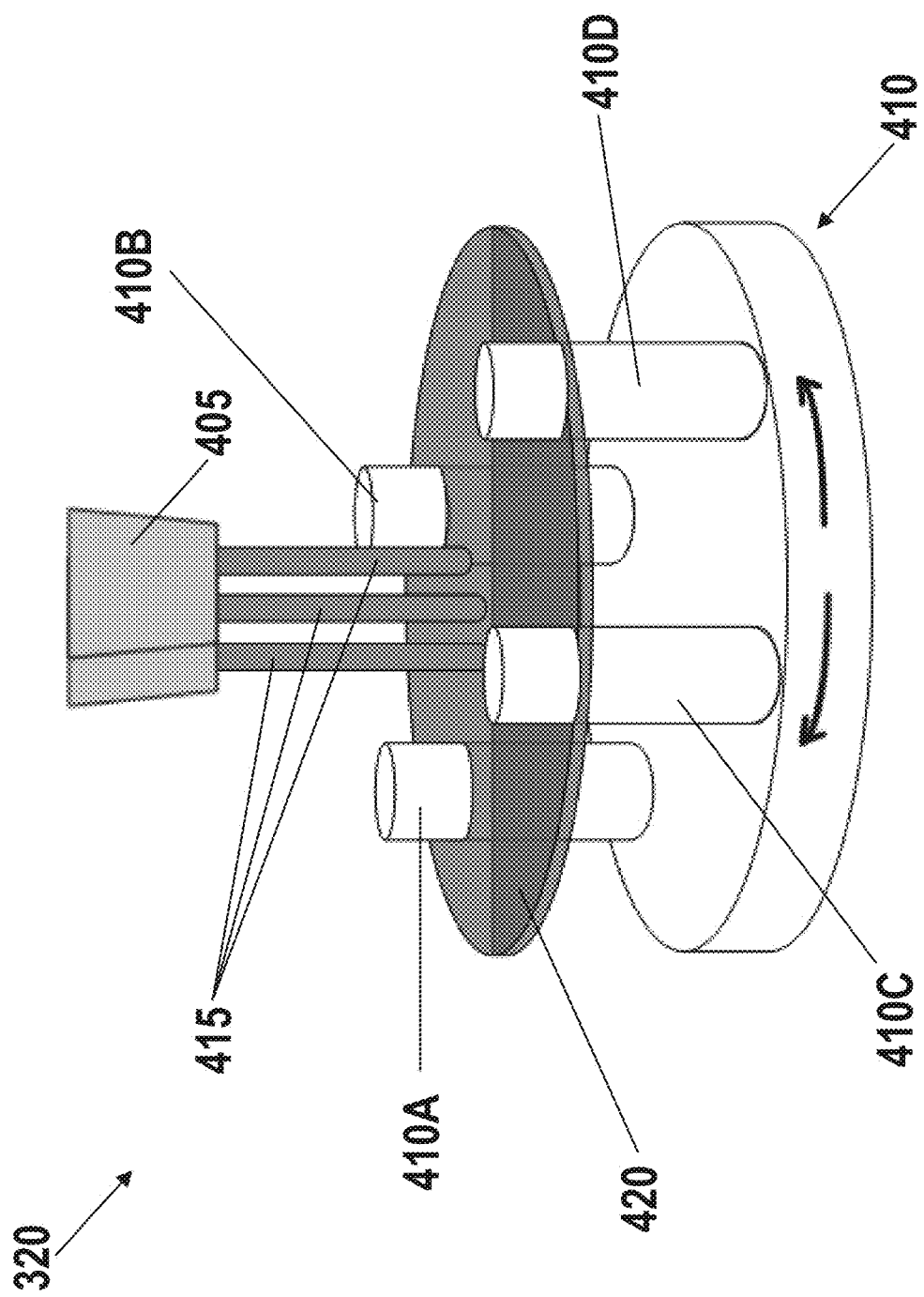
FIG. 4 depicts an example alignment mechanism which may be used in some embodiments of the present invention.

FIG. 4 depicts an example alignment mechanism 320 where a sensor 405 is connected to a printed circuit board (PCB) 420 via rigid structures 415 (e.g., rigid tubing). The PCB 420 in this example has 4 holes which receives extension components 410A, 410B, 410C, and 410D of a rotational piezo actuator 410. Thus, as the Rotational Piezo Actuator 410 rotates (in response to a control signal), the PCB 420 rotates. In turn, this causes rotation of the rigid structures 415 and the sensor 405.

The results gathered via monitoring of spatiotemporal magnetic field monitoring can be employed to correct various imperfections and other deviations from ideal conditions that arise during image acquisition. For example, gradient field imperfections are known; therefore, effect of them can be corrected in the image reconstruction. Additionally, the gradient field measurements can be used as a feedback for gradient system itself to correct the gradient system imperfections. Moreover, if the sensors are in physical contact with the patient, patient motion data can be characterized from these field measurements and the effect of patient motion can be corrected in the image post-processing part or sequence itself can be adapted to such motions in real time.

Figure 5:
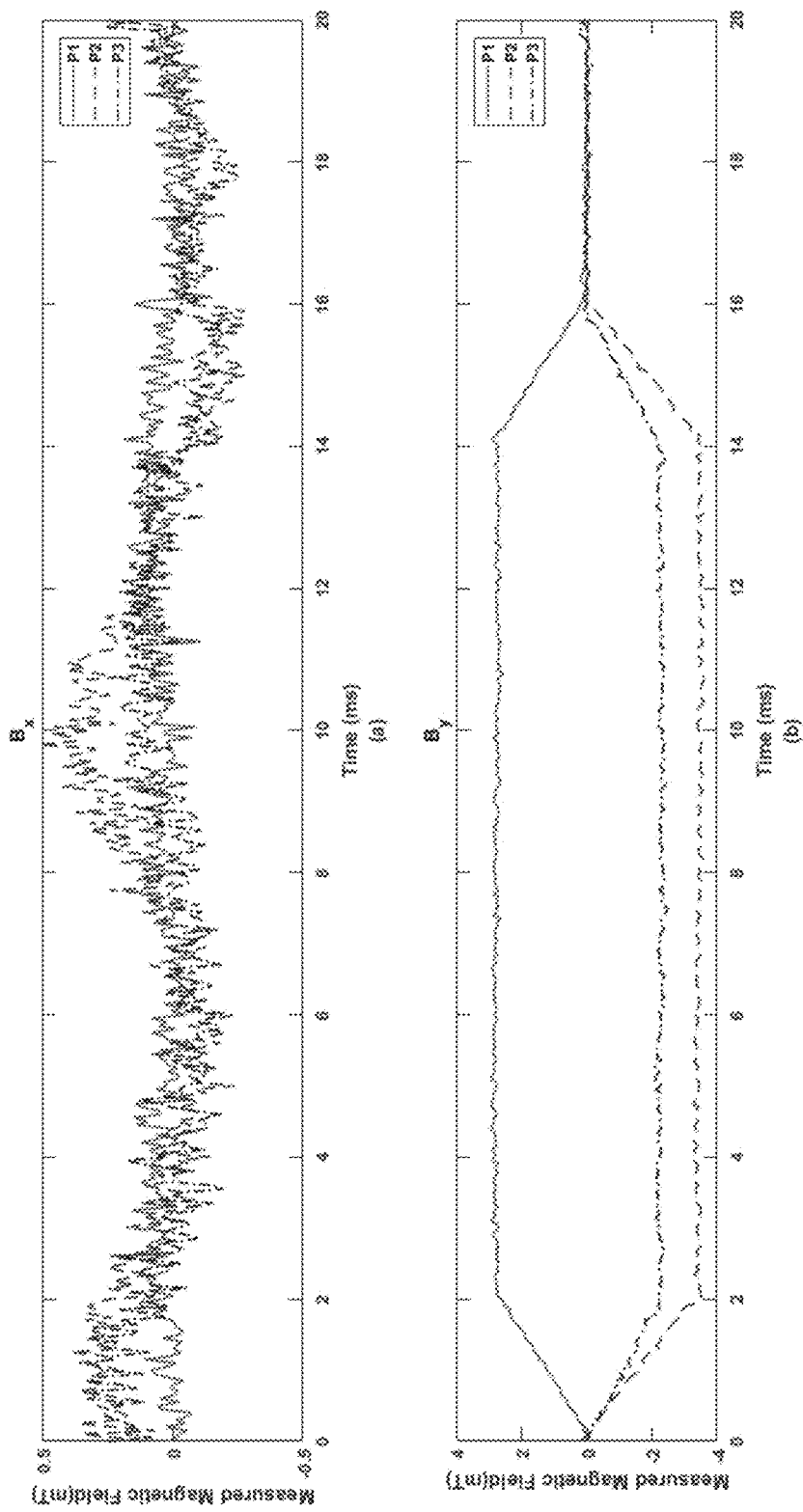
FIG. 5 shows measured sensor output voltages, as generated in one implementation of the techniques described herein.
Figure 6:
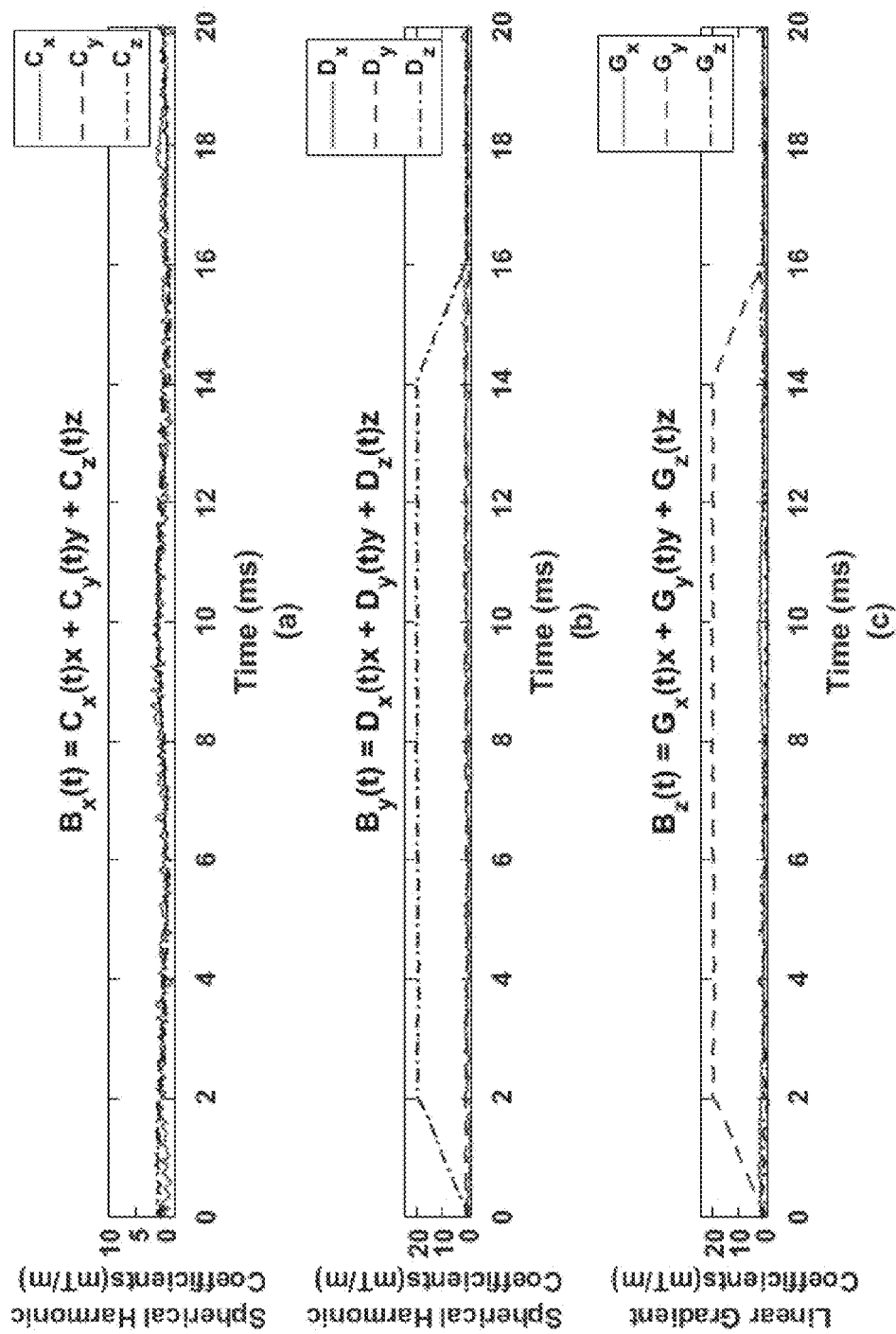
FIG. 6 shows the reconstructed first order spherical harmonic coefficients in 3 axes, as generated in one implementation of the techniques described herein.

FIGS. 5 and 6 show the results of experiments performed with a 3T MRI Scanner (Tim Trio, Siemens). To demonstrate the proof of concept, sensors are placed at 3 different positions in 3 different scans. At each scan, y-gradient is applied with strength of 20 mT/m, rise and fall times of 2 ms and flat top duration of 12 ms.

FIG. 5 shows the measured sensor output voltages, as converted to magnetic field. The top plot shows $B_x$, the x component of the magnetic field, while the bottom plot shows $B_y$, the y component of the magnetic field. Measurements are obtained at 3 different spatial positions to be able to reconstruct first order spherical harmonics.

FIG. 6 shows the reconstructed first order spherical harmonic coefficients along 3 axes. The top plot in FIG. 6 shows the $B_x$, x component of the magnetic field, while the middle plot shows $B_y$, y component of the magnetic field. After $B_x$ and $B_y$ are determined, Bz may be determined using the Equation 1 and 2, as shown in the bottom plot of FIG. 6. The bottom plot also corresponds to linear gradient terms. The dashed line in the $B_z$ plot (labeled "$G_y$") shows the applied y-gradient during sequence with reasonably consistent timing and amplitude. These three plots are sufficient to determine the first order spatial variations of the magnetic field as well as temporal dynamics.

Figure 7:
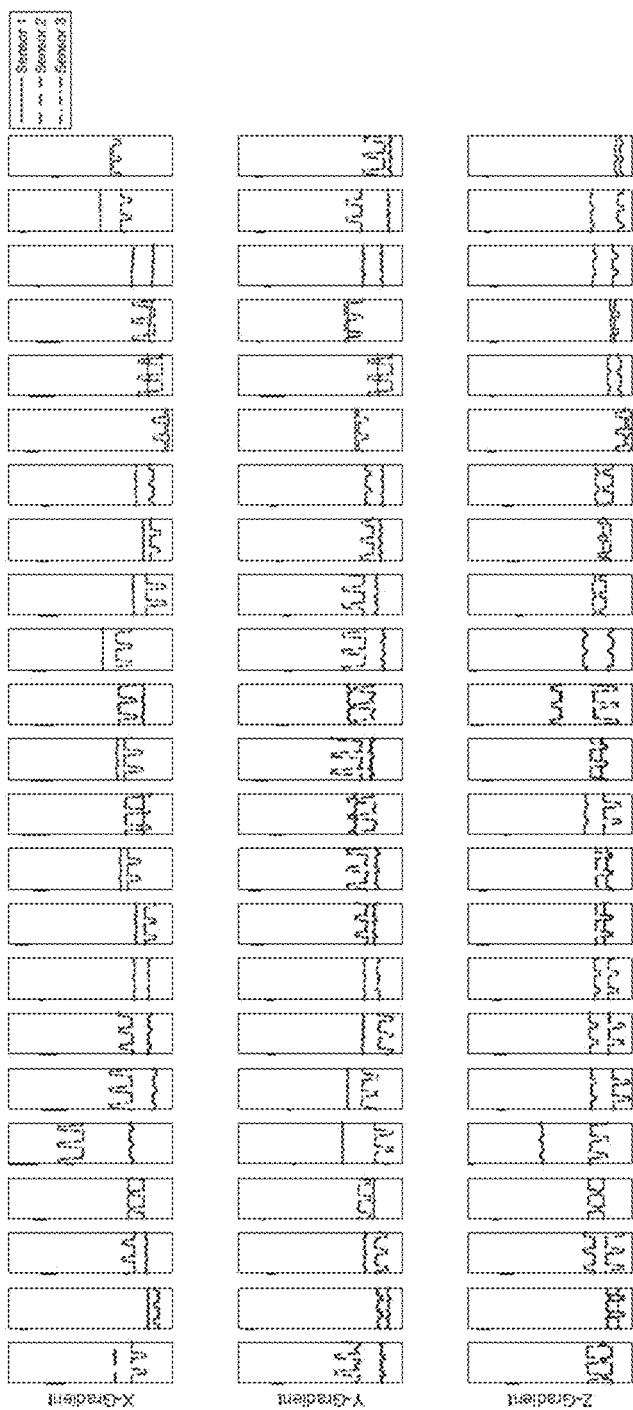
FIG. 7 shows Hall effect sensor outputs, as generated in one implementation of the techniques described herein.

FIG. 7 shows Hall effect sensor outputs. Each individual plot (shown in different shades of gray) is output for a different sensor. Sensors 1 and 3 are sensitive to magnetic field in the same direction. Each row shows the waveform for different applied gradient direction. As shown in this data, three different spatial locations are sufficient to calculate the first order field distribution; however, higher order spherical harmonics can also be calculated from the data.

Figure 8:
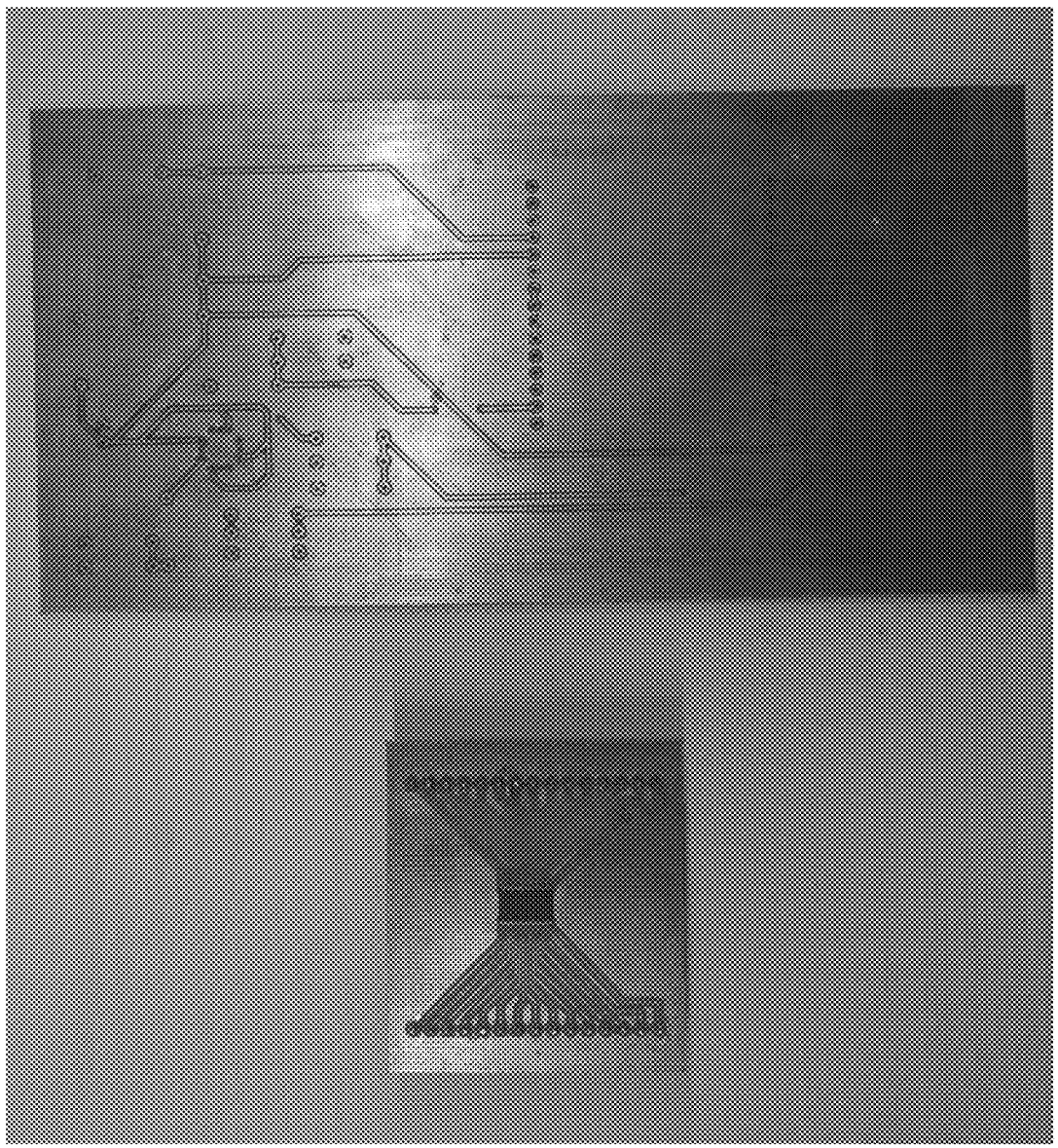
FIG. 8 shows analog-to-digital converter and printed circuit board, that may be employed in different embodiments of the present invention.

In order to digitize the data, an Analog to Digital Converter ("ADC") with enough temporal resolution and signal-to-noise ratio ("SNR") should be used. ADC frequency can be determined by the cutoff frequency of the low pass filter at the output of the sensor and this cutoff frequency should be determined according to noise level of the sensor and required SNR of the gradient field measurements. There is a trivial tradeoff between bandwidth of the sensors and SNR of the magnetic field measurements. Ideally, the ADC should be placed near the sensors as much as possible because eddy current due to E-fields can cause undesired voltage induction in the output cables of the sensors and digitizing the data directly next to sensors is beneficial to minimize the E-field effect. After digitizing the data, data can be carried to processing unit as optical, low-voltage differential signaling ("LVDS") or using conventional methods depending on the required data speed, noise level and distance. Also the ADC can be used in a time multiplexed manner to better occupy the bandwidth. In other words, any parallel acquisition of the data from the sensors can be employed. FIG. 8 shows a 4 channel interleaved ADC (left-hand side) and a PCB (right-hand side) to integrate Hall effect sensors with ADC and other supporting circuits.

Figure 9B:
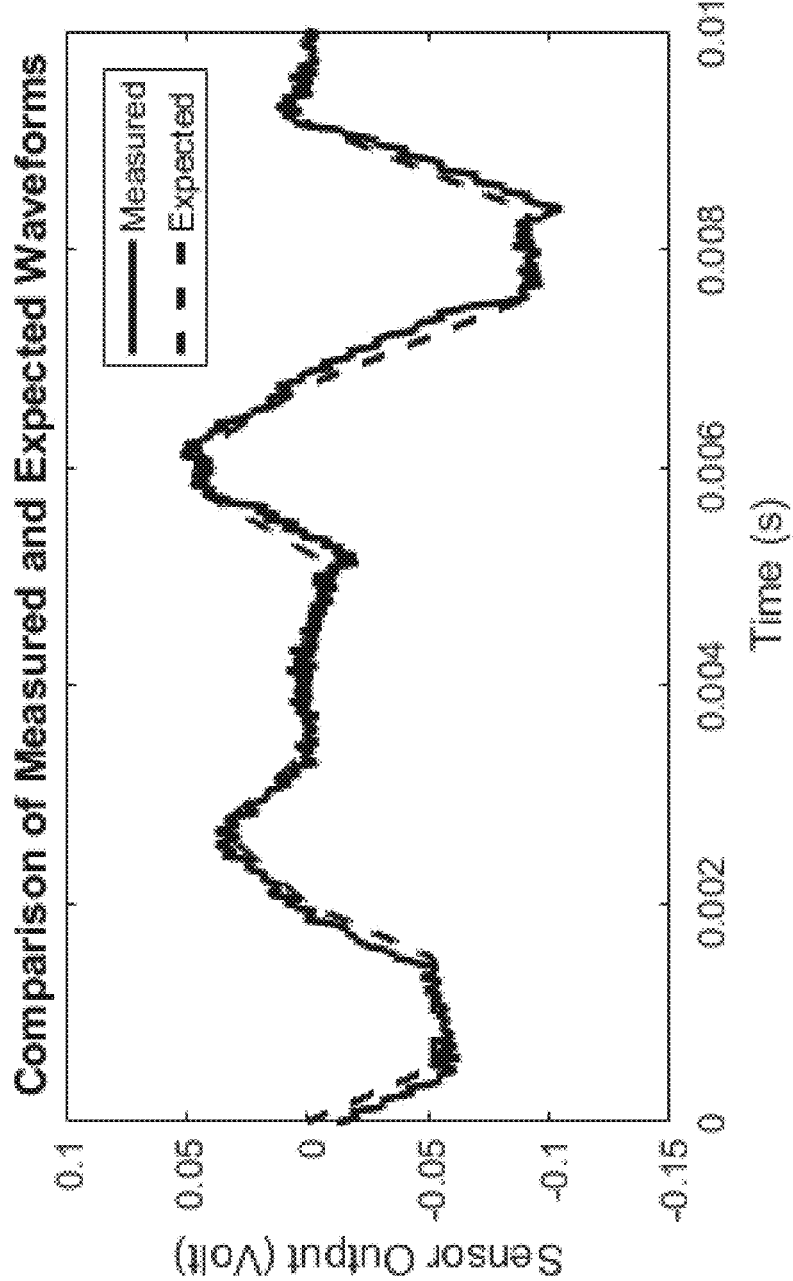
FIG. 9B shows expected waveforms and the measured waveforms for each sensor, as generated in one implementation of the techniques described herein.

In one example implementation of the techniques described herein, sensors were placed at certain locations in the bore of the MRI scanner and a calibration gradient waveform was applied in each direction. In order to neglect frequency dependent errors, sensor outputs were measured when calibration gradient waveforms were at the flat top. Furthermore, data was acquired with much higher bandwidth than the sensors have; therefore data was digitally low-pass filtered. Example calibration data and low pass filtered results are shown in FIG. 9A. A fast gradient waveform including 3 gradient axes was applied and the applied gradient waveform was estimated from the calibration data. FIG. 9B shows expected waveforms and the measured waveforms for each sensor. Note that the good match between expected and measured signals verifies that the measurement techniques described herein are linear and time-invariant.

FIG. 10 is a block diagram illustrating an MRI scanner system 1000 according to an embodiment of the present disclosure. The MRI scanner system 1000 includes a gantry 20, a signal transceiving unit 30, a monitoring unit 40, a system control unit 50, and an operating unit 60. The gantry 20 blocks electromagnetic waves generated by a main magnet 22, a gradient coil 24, an RF coil 26, etc. from being radiated to the outside. The hollow interior portion of the gantry 20 is referred to as the "bore." An electromagnetic field and a gradient magnetic field may be formed in the bore and an RF signal may be irradiated from the bore toward an object 10.

The main magnet 22, the gradient coil 24, and the RF coil 26 are disposed in a predetermined direction of the gantry 20. The predetermined direction may include a coaxial cylindrical direction, or the like. The object 10 may be positioned on a table 28 insertable into a cylinder along a horizontal axis of the cylinder. The main magnet 22 may generate a static magnetic field for aligning a magnetic dipole moment of the atomic nuclei included in the object 10 in a predetermined direction. As the magnetic field generated by the main magnet is stronger and more uniform, a relatively precise and accurate MR image with respect to the object 10 may be obtained.

The gradient coil 24 includes X, Y, and Z coils that generate gradient magnetic fields in mutually orthogonal X-, Y-, and Z-axis directions. The gradient coil 24 may provide positional information of each part of the object 10 by inducing resonance frequencies differently for each part of the object 10.

The RF coil 26 irradiates RF signals to a patient and receives magnetic resonance signals emitted from the patient. For example, the RF coil 26 may transmit an RF signal having a frequency equal to a frequency of a processional motion toward the atomic nucleus which performs the processional motion to the patient and thereafter, stop transmission of the RF signal and receive the magnetic resonance signal emitted from the patient. For example, the RF coil 26 may generate an electromagnetic signal, having a radio frequency corresponding to the type of atomic nucleus, for example, an RF signal, and apply the generated RF signal to the object 10 so as to transition a certain atomic nucleus from a low energy state to a high energy state. When the electromagnetic signal generated by the RF coil 26 is applied to the certain atomic nucleus, the certain atomic nucleus may transition from the low energy state to the high energy state. Thereafter, when the electromagnetic wave generated by the RF coil 26 is removed, the atomic nucleus to which the electromagnetic wave has been applied may emit electromagnetic waves having a Larmor frequency while transitioning from the high energy state to the low energy state. In other words, when the application of the electromagnetic signal to the atomic nucleus is interrupted, and the atomic nucleus to which the electromagnetic wave is applied transitions from a high-energy state to a low-energy state, the electromagnetic wave having the Larmor frequency may be emitted. Here, the Larmor frequency may mean a frequency at which magnetic resonance is induced in the atomic nucleus.

The RF coil 26 receives the electromagnetic signals irradiated from the atomic nuclei inside the object 10. The RF coil 26 may be implemented as one RF transceiving coil having both a function of generating the electromagnetic wave having the radio frequency corresponding to the type of the atomic nucleus and a function of receiving the electromagnetic waves irradiated from the atomic nucleus. Further, the RF coil 26 may be implemented as each of a transmission RF coil having the function of generating the electromagnetic wave having the radio frequency corresponding to the type of atomic nucleus and a reception RF coil having the function of receiving the electromagnetic wave irradiated from the atomic nucleus.

Further, the RF coil 26 may be fixed to the gantry 20 and may be removable. The removable RF coil 26 may include RF coils for a portion of the object including a head RF coil, a thorax RF coil, a leg RF coil, a neck RF coil, a shoulder RF coil, a wrist RF coil, and an ankle RF coil. The RF coil 26 may communicate with an external device by a wired and/or wireless manner and may perform even dual tune communication according to a communication frequency band. The RF coil 26 may include RF coils of various channels such as 16 channels, 32 channels, 72 channels, and 144 channels.

The gantry 20 may include a display 29 positioned outside the gantry 20 and a display (not illustrated in FIG. 10) positioned inside the gantry 20. Predetermined information may be provided to the user or the object via the displays positioned inside and outside of the gantry 20.

The signal transceiving unit 30 controls a gradient magnetic field formed in the gantry 20 according to a predetermined MR sequence and control transmission and reception of the RF signal and the magnetic resonance signal. The signal transceiving unit 30 includes a gradient amplifier 32, a transceiving switch 34, an RF transmitting unit 36, and an RF receiving unit 38.

The gradient amplifier 32 may drive the gradient coil 24 included in the gantry 20 and supply a pulse signal for generating the gradient magnetic field to the gradient coil 24 under the control of the gradient magnetic field control unit 54.

The gradient magnetic field control unit 54 may control the pulse signal supplied from the gradient amplifier 32 to the gradient coil 24. By controlling the pulse signal supplied to the gradient coil 24, the gradient magnetic fields in X-axis, Y-axis, and Z-axis directions may be synthesized. The pulse signal may be implemented by current.

The RF transmitting unit 36 and the RF receiving unit 38 may drive the RF coil 26. The RF transmitting unit 36 may supply the RF pulse of the Larmor frequency to the RF coil 26 and the RF receiving unit 38 may receive the magnetic resonance signal received by the RF coil 26.

The transceiving switch 34 adjusts transmission/reception directions of the RF signal and the magnetic resonance signal. For example, the transceiving switch 34 may cause the RF signal to be irradiated to the object 10 through the RF coil 26 during a transmission mode and the magnetic resonance signal from the object 10 through the RF coil 26 to be received during a reception mode. The transceiving switch 34 may be controlled by a control signal from an RF control unit 56.

The monitoring unit 40 monitors or controls the gantry 20 or devices mounted on the gantry 20. The monitoring unit 40 includes a system monitoring unit 42, an object monitoring unit 44, a table control unit 46, and a display control unit 48.

The system monitoring unit 42 may monitor and control a state of the static magnetic field, the state of the gradient magnetic field, the state of the RF signal, the state of the RF coil, the state of a table, the state of a device for measuring body information of the object, a power supply state, the state of a heat exchanger, the state of a compressor, and the like.

The object monitoring unit 44 may monitor the state of the object 10. For example, the object monitoring unit 44 includes a camera for observing a motion or a position of the object 10, a respiration measuring unit for measuring respiration of the object 10, an ECG measurer for measuring an electrocardiogram of the object 10, or a body temperature measurer for measuring a body temperature of the object 10.

The table control unit 46 may control movement of the table 28 at which the object 10 is positioned. The table control unit 46 may control the movement of the table 28 according to sequence control of the sequence control unit 52. For example, in moving imaging of the object, the table control unit 46 may continuously or intermittently move the table 28 according to the sequence control by the sequence control unit 52 to thereby photograph the object in a field of view (FOV) larger than the FOV of the gantry.

The display control unit 48 may control the displays positioned outside and inside the gantry 20. For example, the display control unit 48 may control on/off of the displays positioned outside and inside the gantry 20 or a screen to be output to the display. Further, when a speaker is positioned inside or outside the gantry 20, the display control unit 48 may control the on/off of the speaker or a sound to be output through the speaker.

The system control unit 50 includes a sequence control unit 52 for controlling a sequence of signals formed in the gantry 20 and a gantry control unit 58 for controlling the devices mounted on the gantry 20.

The sequence control unit 52 includes the gradient magnetic field control unit 54 for controlling the gradient amplifier 32 and the RF control unit 56. The RF control unit 56 may control the RF transmitting unit 36, the RF receiving unit 38, and the transceiving switch 34. The sequence control unit 52 may control the gradient amplifier 32, the RF transmitting unit 36, the RF receiving unit 38, and the transceiving switch 34 according to a pulse sequence received from the operating unit 60. Here, the pulse sequence includes all information required for controlling the gradient amplifier 32, the RF transmitting unit 36, the RF receiving unit 38, and the transceiving switch 34 and may include, for example, information on the intensity, an application time, an application timing, and the like of the pulse signal applied to the gradient coil 24.

The operating unit 60 provides instructions corresponding to the pulse sequence information to the system control unit 50 and control an operation of the entire MRI apparatus. The operating unit 60 includes an image processing unit 62 for processing the magnetic resonance signal received from the RF receiving unit 38, an output unit 64, and an input unit 66.

The image processing unit 62 processes the magnetic resonance signal received from the RF receiving unit 38 to generate magnetic resonance image data for the object 10. The image processing unit 62 may perform various signal processing such as amplification, frequency conversion, phase detection, low frequency amplification, filtering, and the like on the magnetic resonance signal received by the RF receiving unit 38. The image processing unit 62 arranges digital data in k-space data (also referred to as, for example, a Fourier space or a frequency space) of a memory and performs two-dimensional or three-dimensional Fourier transformation of the data to reconfigure the data into image data. Further, the image processing unit 62 may perform synthesis processing or difference arithmetic processing of the image data as necessary. In addition, various signal processing applied to the magnetic resonance signal by the image processing unit 62 may be performed in parallel. For example, a plurality of magnetic resonance signals may be reconfigured into the image data by applying signal processing in parallel to the plurality of magnetic resonance signals received by a multi-channel RF coil.

The output unit 64 may output the image data or the reconfigured image data generated by the image processing unit 62 to the user. In addition, the output unit 64 may output information required for the user to operate the MRI apparatus, such as a UI (user interface), user information, or object information. The output unit 64 may include, for example, a speaker, a printer, a CRT display, an LCD display, a PDP display, an OLED display, an FED display, an LED display, a VFD display, a DLP display, a PFD display, a 3D display, a transparent display, and the like and may include a variety of output devices within other scopes which are apparent to those skilled in the art. The user may input object information, parameter information, a scan condition, the pulse sequence, information on image synthesis and calculation of difference, and the like using the input unit 66. The input unit 66 may include a keyboard, a mouse, a trackball, a voice recognition unit, a gesture recognition unit, a touch screen, and the like and may include various input devices within the other scopes which are apparent to those skilled in the art.

The functions and process steps herein may be performed automatically, wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112(f), unless the element is expressly recited using the phrase "means for."

We claim:

1. A magnetic resonance imaging (MRI) system, comprising:
    a gantry for receiving a subject, said gantry having a longitudinal axis (herein "z-axis");
    a magnet disposed about said gantry for generating a static magnetic field along said longitudinal axis of the gantry;
    a first gradient magnet for generating a gradient magnetic field along said longitudinal axis;
    a second gradient magnet for generating a gradient magnetic field along a first transverse direction (herein "x-axis") orthogonal said longitudinal axis;
    a third gradient magnet for generating a gradient magnetic field along a second transverse direction (herein "y-axis") orthogonal to said longitudinal axis and said first transverse direction;
    a plurality of magnetic sensors positioned relative to the gantry for measuring gradients of transverse components of magnetic field along one or more of the x, y and z axes, said magnetic sensors generating signals indicative of said measured transverse magnetic field gradients; and
    a controller for receiving said signals and operating on said signals to determine gradients of the gradient magnetic field along said longitudinal axis.

2. The MRI system of claim 1, wherein said magnetic sensors comprise Hall effect sensors.

3. The MRI system of claim 1, wherein said controller determines said longitudinal magnetic field gradients for said at least one location by using the following relations:

$$\frac{\partial B_z}{\partial y} = \frac{\partial B_y}{\partial z}$$
$$\frac{\partial B_z}{\partial x} = \frac{\partial B_x}{\partial z}$$
$$\frac{\partial B_z}{\partial z} = -\left(\frac{\partial B_x}{\partial x} + \frac{\partial B_y}{\partial y}\right)$$

wherein, $$\frac{\partial B_z}{\partial y}$$

denotes gradient of z-component of magnetic field along y-axis, $$\frac{\partial B_y}{\partial z}$$

denotes gradient of y-component of magnetic field along z-axis, $$\frac{\partial B_z}{\partial x}$$

denotes gradient of z-component of magnetic field along x-axis $$\frac{\partial B_z}{\partial z}$$

denotes gradient of z-component of magnetic field along z-axis, $$\frac{\partial B_x}{\partial x}$$

denotes gradient of x-component of magnetic field along x-axis, and $$\frac{\partial B_y}{\partial y}$$

denotes gradient of y-component of magnetic field along y-axis.

4. The MRI system of claim 1, wherein said controller receives calibration signals from said plurality of sensors in absence of applied magnetic fields and employs said calibration signals for calibrating said magnetic sensors.

5. The MRI system of claim 1, further comprising a mechanical holder to which said plurality of magnetic sensors can be mounted, said mechanical holder being positioned relative to said gantry and being configured to provide coordinates of each of said plurality of magnetic sensors along x, y, and z-axes.

6. The MRI system of claim 1, further comprising at least one alignment mechanism for aligning at least one of said plurality of magnetic sensors along any of said x and y-axes for measuring magnetic fields along said axes.

7. The MRI system of claim 6, wherein said at least one alignment mechanism comprises a piezoelectric actuator coupled to said at least one of said plurality of magnetic sensors.

8. The MRI system of claim 7, wherein said at least one alignment mechanism operates under control of said controller.

9. The MRI system of claim 8, wherein said controller instructs said alignment mechanism to adjust an orientation of said at least one sensor based on an output voltage signal generated by said least one sensor.

10. The MRI system of claim 9, wherein said alignment mechanism is configured to rotate said sensor in response to a control signal from said controller so as to align said at least one sensor along on of said x and y-axes.

11. A method for measuring a gradient magnetic field in a magnetic resonance system, comprising:
    positioning a plurality of magnetic sensors relative to a longitudinal axis (herein "z-axis") of a gantry;
    using the plurality of magnetic sensors to collect measurements indicative of:
        a measurement of a gradient magnetic field along a first transverse direction (herein "x-axis") orthogonal to the longitudinal axis, and a measurement of a gradient magnetic field along a second transverse direction (herein "y-axis") orthogonal to the longitudinal axis and the first transverse direction;

determining a measurement of a gradient magnetic field along the z-axis based on the measurement of the gradient magnetic field along the x-axis and the measurement of a gradient magnetic field along the y-axis.

12. The method of claim 11, wherein the magnetic sensors comprise Hall effect sensors.

13. The method of claim 11, wherein the plurality of magnetic sensors is located within a mechanical holder and positioning the plurality of magnetic sensors relative to the z-axis comprises:

aligning the mechanical holder with the z-axis.

14. The method of claim 13, wherein the mechanical holder is aligned using a piezoelectric actuator.

15. The method of claim 14, wherein the piezoelectric actuator aligns the mechanical holder based on signals generated by the plurality of magnetic sensors.

16. A magnetic resonance imaging (MRI) system, comprising:

a plurality of magnetic sensors positioned relative to a longitudinal axis (herein "z-axis") of a gantry, wherein the plurality of magnetic sensors are configured to collect measurements during an MRI scan comprising:

a measurement of a gradient magnetic field along a first transverse direction (herein "x-axis") orthogonal to the longitudinal axis, and a measurement of a gradient magnetic field along a second transverse direction (herein "y-axis") orthogonal to the longitudinal axis and the first transverse direction; and one or more computers configured to determine a measurement of a gradient magnetic field along the z-axis based on the measurement of the gradient magnetic field along the x-axis and the measurement of the gradient magnetic field along the y-axis.

17. The MRI system of claim 16, wherein the y-axis is orthogonal the x-axis.

18. The MRI system of claim 16, wherein the one or more computers are further configured to:

estimate a k-space trajectory of the MRI scan based on the measurement of the gradient magnetic field along the x-axis and the measurement of the gradient magnetic field along the y-axis; and use the k-space trajectory to reconstruct one or more images based on k-space data acquired during the MRI scan.

19. The MRI system of claim 17, wherein the one or more computers are further configured to:

estimate patient motion data based on the measurement of the gradient magnetic field along the x-axis and the measurement of the gradient magnetic field along the y-axis; and using the patient motion data to perform motion correction on the one or more images.

20. The MRI system of claim 16, wherein the plurality of magnetic sensors are Hall effect sensors.

* * * * *